(12) United States Patent
Lee et al.

(10) Patent No.: US 9,221,922 B2
(45) Date of Patent: *Dec. 29, 2015

(54) METALLOCENE COMPOUND, CATALYST COMPOSITION COMPRISING THE SAME, AND AN OLEFINIC POLYMER PRODUCED USING THE SAME

(71) Applicant: LG CHEM, LTD., Seoul (KR)

(72) Inventors: Yong-Ho Lee, Incheon (KR); Man-Seong Jeon, Daejeon (KR); Ki-Soo Lee, Daejeon (KR); Heon-Yong Kwon, Daejeon (KR); Min-Seok Cho, Daejeon (KR); Jong-Sang Park, Daejeon (KR); Joon-Hee Cho, Daejeon (KR); Hyeon-Gook Kim, Daejeon (KR); Eun-Kyoung Song, Daejeon (KR); Seon-Kyoung Kim, Daejeon (KR); Dae-Sik Hong, Gunpo-si (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/077,896

(22) Filed: Nov. 12, 2013

(65) Prior Publication Data

US 2014/0066288 A1 Mar. 6, 2014

Related U.S. Application Data

(63) Continuation of application No. 13/386,620, filed as application No. PCT/KR2010/004991 on Jul. 29, 2010, now Pat. No. 8,692,009.

(30) Foreign Application Priority Data

Jul. 31, 2009 (KR) .................. 10-2009-0070574
Jul. 28, 2010 (KR) .................. 10-2010-0072934

(51) Int. Cl.
| | | |
|---|---|---|
| C07F 17/00 | (2006.01) | |
| C08F 4/642 | (2006.01) | |
| C08F 4/643 | (2006.01) | |
| C08F 4/6592 | (2006.01) | |
| C08F 4/76 | (2006.01) | |
| C08F 10/00 | (2006.01) | |
| C08F 4/659 | (2006.01) | |
| C08F 210/16 | (2006.01) | |

(52) U.S. Cl.
CPC . *C08F 4/76* (2013.01); *C07F 17/00* (2013.01); *C08F 4/65927* (2013.01); *C08F 10/00* (2013.01); *C08F 4/65912* (2013.01); *C08F 210/16* (2013.01)

(58) Field of Classification Search
CPC ............ C08F 4/65927; C08F 4/65908; C08F 4/65912; C07F 17/00

USPC ............ 556/53; 502/103, 152; 526/126, 133, 526/134, 160, 165, 943
See application file for complete search history.

(56) References Cited

U.S. PATENT DOCUMENTS

| 5,786,495 A | 7/1998 | Resconi et al. |
|---|---|---|
| 6,506,919 B1 | 1/2003 | Oh et al. |
| 8,124,557 B2 | 2/2012 | Lee et al. |
| 2006/0052238 A1 | 3/2006 | Lee et al. |
| 2006/0235171 A1 | 10/2006 | Lee et al. |

FOREIGN PATENT DOCUMENTS

| JP | 06-256369 A | 9/1994 |
|---|---|---|
| JP | 07-149781 A | 6/1995 |
| JP | 08-259583 A | 10/1996 |
| JP | 10-007848 A | 1/1998 |
| JP | 10-025376 A | 1/1998 |
| JP | 2000-309605 A | 11/2000 |
| JP | 2001-122886 A | 5/2001 |
| JP | 2006-509904 A | 3/2006 |
| JP | 2006-213770 A | 8/2006 |
| JP | 2007-519781 A | 7/2007 |
| JP | 2007-246433 A | 9/2007 |
| KR | 1996-0034231 | 10/1996 |
| KR | 10-2001-0086089 | 9/2001 |
| KR | 10-2006-0021476 | 3/2006 |
| KR | 10-2007-0114696 | 12/2007 |

OTHER PUBLICATIONS

H. G. Alt, et al.; "Polymerization of Ethylene With Metallocene/ Methylaluminoxane Catalysts Supported on Polysiloxane Micro Gels and Silica" 1996, 568, pp. 263-269.

K. Patsidis et al., The Synthesis, Characterization and Polymerization Behavior of Ansa Cyclopentadienyl Fluorenyl Complexes...; Journal of Organometallic Chemistry, 1996, 509, pp. 63-71.

Resconi, L., et al., "Selectively in Propene Polymerization with Mwtallocene Catalysts," Chemical Reviews, 2000, vol. 100, No. 4, pp. 1253-1345.

*Primary Examiner* — Caixia Lu
(74) *Attorney, Agent, or Firm* — Dentons US LLP

(57) ABSTRACT

The present invention relates to a novel metallocene compound, a catalyst composition comprising the same, and to olefinic polymers produced using the same. The metallocene compound according to the present invention and the catalyst composition comprising the same can be used when producing olefinic polymers, have outstanding copolymerization properties, and can produce olefinic polymers of high molecular weight. In particular, when the metallocene compound according to the present invention is employed, highly heat resistant block copolymers can be produced, and olefinic polymers can be produced which have a high melting point (Tm) even if the comonomer content is increased when producing the olefinic polymer.

4 Claims, 2 Drawing Sheets

METALLOCENE COMPOUND, CATALYST COMPOSITION COMPRISING THE SAME, AND AN OLEFINIC POLYMER PRODUCED USING THE SAME

This application is a Continuation of U.S. patent application Ser. No. 13/386,620 filed Jan. 23, 2012 which is the U.S. National Phase application of International Application No. PCT/KR2010/004991, filed Jul. 29, 2010 and claims the benefit of Korean Application Nos. 10-2009-0070574 filed on Jul. 31, 2009 and 10-2010-0072934, filed Jul. 28, 2010, all of which are hereby incorporated by reference in their entirety for all purposes as if fully set forth herein.

TECHNICAL FIELD

The present invention relates to a novel metallocene compound, a catalyst composition comprising the same, and an olefinic polymer prepared by using the same.

BACKGROUND ART

Dow Co. had presented [Me$_2$Si(Me$_4$C$_5$)NtBu]TiCl$_2$ (Constrained-Geometry Catalyst, hereinafter 'CGC') in the early 1990's (U.S. Pat. No. 5,064,802), the superior aspects of the CGC to prior known metallocene catalysts in copolymerization reaction of ethylene and α-olefin can be largely summarized into two ways as follows: (1) it shows high activity even in high polymerization temperature and forms a polymer of high molecular weight, (2) the copolymerizing ability of α-olefin such as 1-hexene and 1-octene which have large steric hindrance is also very excellent. As various characteristics in the polymerization reaction of the CGC became gradually known, there have been many efforts to synthesize derivatives of the same for using it as a polymerization catalyst in the academic world and the industrial world.

Group 4 transition metal compound which has one or two cyclopentadienyl groups as the ligand can be used as a catalyst for olefin polymerization by activating the same with methylaluminoxane or a boron compound. Such catalyst shows unique characteristics that traditional Zeigler-Natta catalyst cannot realize.

Namely, the polymer obtained by using such catalyst has narrow molecular weight distribution and more good reactivity to the second monomer such as α-olefin or cycloolefin, and the second monomer distribution in the polymer is even. Furthermore, it is possible to control the stereoselectivity of the polymer in the polymerization of α-olefin by changing the substituent of the cyclopentadienyl ligand in the metallocene catalyst, and when copolymerizing ethylene and other olefins, the degree of copolymerization, the molecular weight, and the distribution of the second monomer can be easily controlled.

Meanwhile, since the metallocene catalyst is more expensive than Zeigler-Natta catalyst, it must have good activity for its economic value. If it has good reactivity to the second monomer, there is an advantage of that the polymer including large content of the second monomer can be obtained by using only small amount of the second monomer.

As the results that many researchers have studied various catalysts, it is proved that generally a bridged catalyst has good reactivity to the second monomer. The bridged catalyst developed until now can be classified into three types according the type of the bridge. The first type is the catalyst of which two cyclopentadienyl ligands are connected with an alkylene dibridge by the reaction of an electrophile like an alkyl halide and indene or fluorene, the second type of the silicone-bridged catalyst of which the ligands are connected with —SiR$_2$—, and the third type is the methylene-bridged catalyst which is obtained by the reaction of fulvene and indene or fluorene.

However, very few catalysts have been being applied in practice in commercial factories among above attempts, and thus the preparation of catalyst showing more improved polymerization performance is still required.

SUMMARY OF THE INVENTION

It is an aspect of the present invention to provide a metallocene compound which has superior copolymerizing ability and can form an olefinic polymer having high molecular weight, a catalyst composition comprising the same, and a method of preparing an olefinic polymer by using the same.

The present invention provides a metallocene compound represented by following Chemical Formula 1:

[Chemical Formula 1]

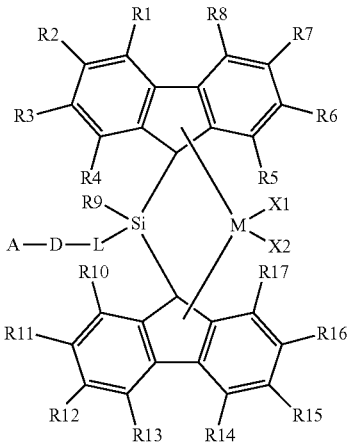

wherein,

R1 to R17 are same or different each other, and are independently hydrogen, a halogen, a C$_1$~C$_{20}$ alkyl group, a C$_2$~C$_{20}$ alkenyl group, a C$_6$~C$_{20}$ aryl group, a C$_7$~C$_{20}$ alkylaryl group, or a C$_7$~C$_{20}$ arylalkyl group, L is a C$_1$~C$_{10}$ linear or branched alkylene group, D is —O—, —S—, —N(R)—, or —Si(R)(R')—, wherein R and R' are same or different each other, and are independently hydrogen, a halogen, a C$_1$~C$_{20}$ alkyl group, a C$_2$~C$_{20}$ alkenyl group, or a C$_6$~C$_{20}$ aryl group, A is hydrogen, a halogen, a C$_1$~C$_{20}$ alkyl group, a C$_2$~C$_{20}$ alkenyl group, a C$_6$~C$_{20}$ aryl group, a C$_7$~C$_{20}$ alkylaryl group, or a C$_7$~C$_{20}$ arylalkyl group, a C$_1$~C$_{20}$ alkoxy group, a C$_2$~C$_{20}$ alkoxyalkyl group, a C$_2$~C$_{20}$ heterocycloalkyl group, or a C$_5$~C$_{20}$ heteroaryl group, M is a group 4 transition metal, X1 and X2 are, same or different each other, and are independently a halogen, a C$_1$~C$_{20}$ alkyl group, a C$_2$~C$_{20}$ alkenyl group, a C$_6$~C$_{20}$ aryl group, a nitro group, an amido group, a C$_1$~C$_{20}$ alkylsilyl group, a C$_1$~C$_{20}$ alkoxy group, or a C$_1$~C$_{20}$ sulfonate group.

The present invention also provides a catalyst composition comprising the metallocene compound.

The present invention also provides a method of preparing an olefinic polymer comprising the step of polymerizing olefinic monomers in the presence of the catalyst composition.

The metallocene compound according to the present invention and the catalyst composition comprising the same can be used when producing olefinic polymers, have outstanding copolymerisation properties, and can produce olefinic polymers of high molecular weight. In particular, when the metallocene compound according to the present invention is employed, highly heat resistant block copolymers can be produced, and olefinic polymers can be produced which have a high melting point (Tm) even if the comonomer content is increased when producing the olefinic polymer.

DETAILED DESCRIPTION OF THE EMBODIMENTS

Figure 1:
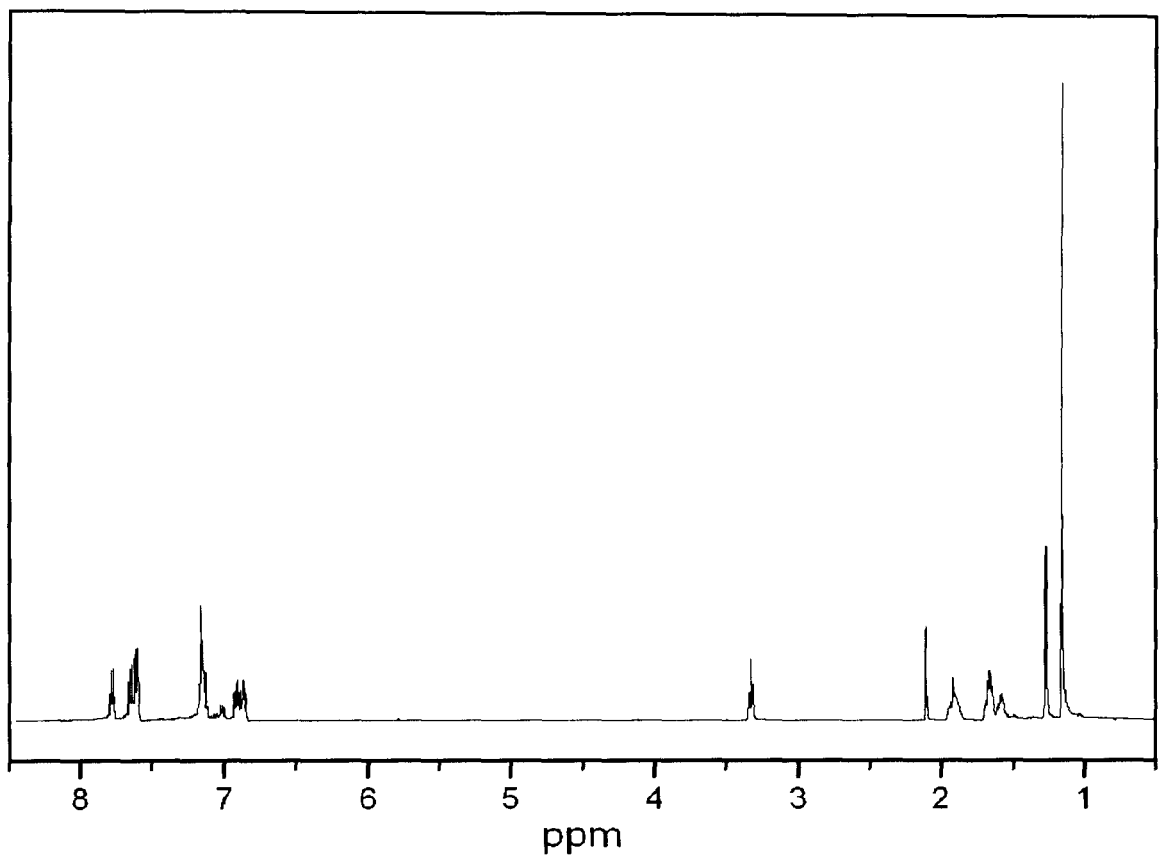
FIG. 1 represents $^1$H NMR result of the metallocene compound prepared according to Preparation Example 1 of the present invention.
Figure 2:
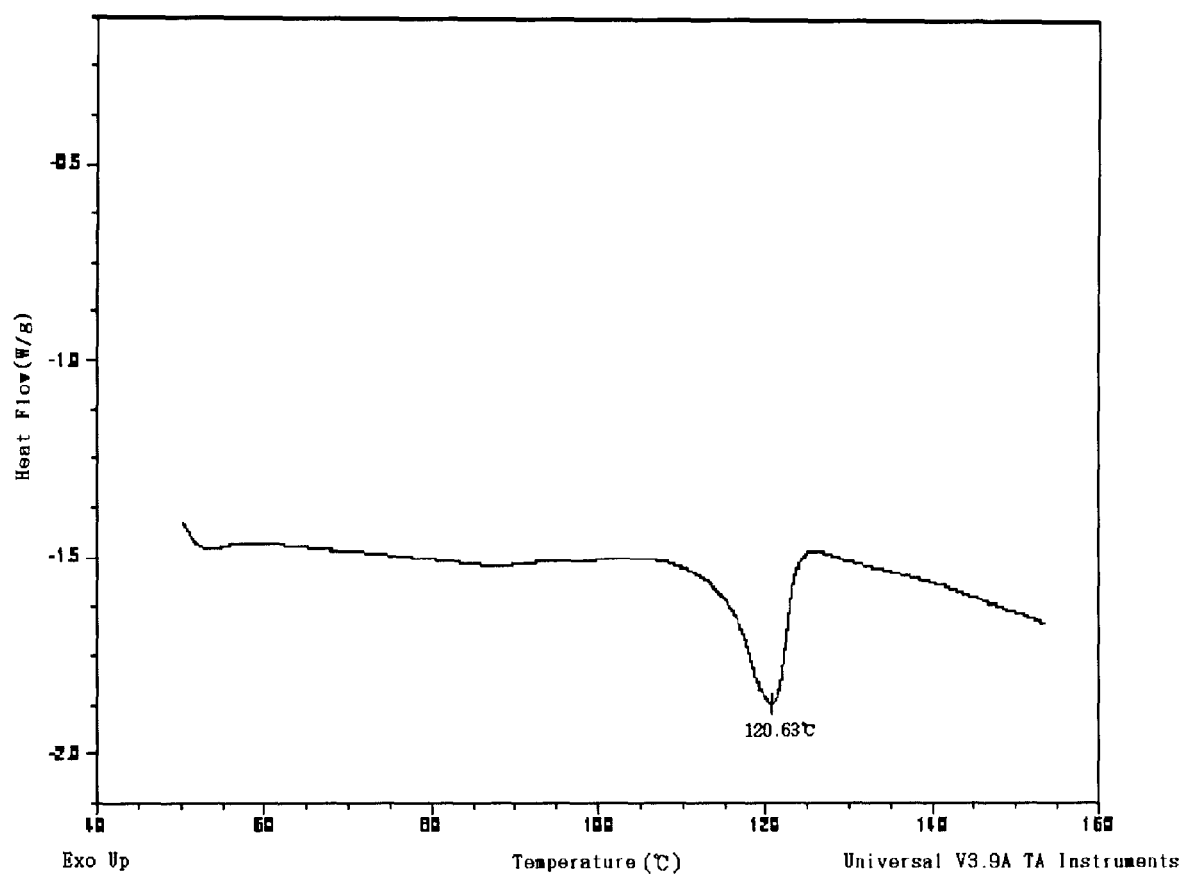
FIG. 2 represents DSC result of the ethylene/α-olefin polymer prepared according to Example 1 of the present invention.

Hereinafter, the present invention is explained in more detail.

The methallecene compound according to the present invention is characterized in that it is represented by above Chemical Formula 1.

In the metallocene compound of the present invention, the substitutents of Chemical Formula 1 are more specifically explained as follows.

The $C_1\sim C_{20}$ alkyl group may be linear or branched alkyl group, and specifically methyl group, ethyl group, propyl group, isopropyl group, n-butyl group, tert-butyl group, pentyl group, hexyl group, heptyl group, octyl group, and the like, however, it is not limited to them.

The $C_2\sim C_{20}$ alkenyl group may be linear or branched alkenyl group, and specifically allyl group, ethenyl group, propenyl group, butenyl group, pentenyl group, and the like, however, it is not limited to them.

The $C_6\sim C_{20}$ aryl group may be linear or branched aryl group, and specifically phenyl group, biphenyl group, naphthyl group, phenanthrenyl group, fluorenyl group, and the like, however, it is not limited to them.

The $C_5\sim C_{20}$ heteroaryl group may be a single ring heteroaryl group or a condensed ring heteroaryl group, and specifically carbazolyl group, pyridyl group, quinoline group, isoquinoline group, thiophenyl group, furanyl group, imidazole group, oxazolyl group, thiazolyl group, triazine group, tetrahydropyranyl group, tetrahydrofuranyl group, and the like, however, it is not limited to them.

The $C_1\sim C_{20}$ alkoxy group may be methoxy group, ethoxy group, phenyloxy group, cyclohexyloxy group, and the like, however, it is not limited to them.

The Group 4 transition metal may be titanium, zirconium, hafnium, and the like, however, it is not limited to them.

In the metallocene compound according to the present invention, it is preferable that R1 to R17 in Chemical Formula 1 are independently hydrogen, methyl group, ethyl group, propyl group, isopropyl group, n-butyl group, tert-butyl group, pentyl group, hexyl group, heptyl group, octyl group, or phenyl group, however, it is not limited to them.

In the metallocene compound according to the present invention, it is preferable that L in Chemical Formula 1 is a $C_4\sim C_8$ linear or branched alkylene group, however, it is not limited to them. Furthermore, the alkylene group may be unsubstituted or substituted with a $C_1\sim C_{20}$ alkyl group, a $C_2\sim C_{20}$ alkenyl group, or a $C_6\sim C_{20}$ aryl group.

In the metallocene compound according to the present invention, it is preferable that A in Chemical Formula 1 is hydrogen, methyl group, ethyl group, propyl group, isopropyl group, n-butyl group, tert-butyl group, methoxymethyl group, tert-butoxybutyl group, 1-ethoxyethyl group, 1-methyl-1-methoxyethyl group, tetrahydropyranyl group, or tetrahydrofuranyl group, however, it is not limited to them.

The representative example of the metallocene compound represented Chemical Formula 1 may be the compound of Chemical Formula 2, however, it is not limited to this.

[Chemical Formula 2]

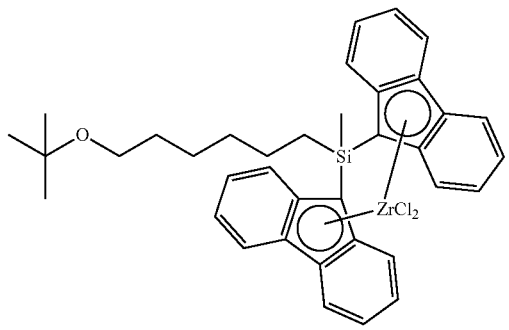

The preparation method of the metallocene compound according to the present invention is concretely disclosed in the following Examples.

The present invention also provides a catalyst composition comprising the metallocene compound.

The catalyst composition according to the present invention may further comprise at least one co-catalysts represented by Chemical Formula 3, Chemical Formula 4, or Chemical Formula 5:

—[Al(R18)-O]$_n$—      [Chemical Formula 3]

wherein,
each R18 may be same or different, and is independently a halogen; a $C_1\sim C_{20}$ hydrocarbon; or a halogen-substituted $C_1\sim C_{20}$ hydrocarbon; and
n is an integer of 2 or more;

D(R18)$_3$      [Chemical Formula 4]

wherein,
R18 is same as that in Chemical Formula 3; and
D is aluminum or boron;

[L-H]$^+$[ZA$_4$]$^-$ or [L]$^+$[ZA$_4$]$^-$      [Chemical Formula 5]

wherein,
L is a neutral or cationic Lewis acid;
H is hydrogen atom;
Z is group 13 element; and
each A may be same or different, and is independently a $C_6\sim C_{20}$ aryl group or a $C_1\sim C_{20}$ alkyl group of which at least one hydrogen atom are unsubstituted or substituted with a halogen, a $C_1\sim C_{20}$ hydrocarbon, an alkoxy, or phenoxy.

Representative example of the compound of Chemical Formula 3 may be methylaluminoxane, ethylaluminoxane, isobutylaluminoxane, butylaluminoxane, and the like, and more preferable compound may be methylaluminoxane.

Representative example of the compound represented by Chemical Formula 4 may be trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminum methoxide, dimethylaluminum ethoxide, trimethylboron, triethylboron, triisobutylboron, tripropylboron, tributylboron, and the like, and more preferable compound may be selected from trimethylaluminum, triethylaluminum, and triisobutylaluminum.

Representative example of the compound of Chemical Formula 5 may be triethylammonium tetraphenylboron, tributylammonium, trimethylammonium tetraphenylboron, tripropylammonium tetraphenylboron, trimethylammonium tetra (p-tolyl)boron, trimethylammonium tetra(o,p-dimethylphenyl)boron, tributyl ammonium tetra(p-trifluoromethylphenyl)boron, trimethyl ammonium tetra(p-trifluoromethylphenyl)boron, tributylammonium tetrapentafluorophenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetrapentafluorophenylaluminum, diethylammonium tetrapentatetraphenylaluminum, triphenylphosphonium tetraphenylaluminum, trimethylphosphonium tetraphenyl aluminum, tripropylammonium tetra(p-tolyl)boron, triethylammonium tetra(o,p-dimethylphenyl)boron, tributylammonium tetra(p-trifluoromethylphenyl)boron, triphenylcarbonium tetra(p-trifluoromethylphenyl)boron, triphenylcarbonium tetrapentafluorophenylboron, and the like.

The catalyst composition according to the present invention may be prepared by the method comprising the steps of 1) contacting the metallocene compound represented by Chemical Formula 1 with the compound represented by Chemical Formula 3 or Chemical Formula 4 and obtaining a mixture; and 2) adding the compound represented by Chemical Formula 5 into the mixture, as the first method.

Furthermore, the catalyst composition according to the present invention may be prepared by the method of contacting the metallocene compound represented by Chemical Formula 1 with the compound represented by Chemical Formula 3, as the second method.

In the first method of preparing the catalyst composition, the mole ratio of the metallocene compound represented by Chemical Formula 1/the compound represented by Chemical Formula 3 or Chemical Formula 4 is preferably 1/5,000~1/2, more preferably 1/1,000~1/10, and still more preferably 1/500~1/20. When the mole ratio of the metallocene compound represented by Chemical Formula 1/the compound represented by Chemical Formula 3 or Chemical Formula 4 is larger than 1/2, there is a problem of that the alkylating agent is very small in quantity and the metal compound is not completely alkylated, and when the mole ratio is lesser than 1/5,000, the alkylation of the metal compound is accomplished but there is a problem of that the alkylated metal compound is not completely activated due to the side reaction between the remaining excess alkylating agent and the activator of Chemical Formula 5. Furthermore, the mole ratio of the metallocene compound represented by Chemical Formula 1/the compound represented by Chemical Formula 5 is preferably 1/25~1, more preferably 1/10~1, and still more preferably 1/5~1. When the mole ratio of the metallocene compound represented by Chemical Formula 1/the compound represented by Chemical Formula 5 is larger than 1, there is a problem of that the activity of the prepared catalyst composition is deteriorated because the activator is relatively small in quantity and the metal compound is not completely activated, and when the mole ratio is lesser than 1/25, the activation of the metal compound is completely accomplished but there is a problem of that the cost of the catalyst composition is not economical or the purity of the polymer prepared by using the same is decreased due to the remaining excess activator.

In the second method of preparing the catalyst composition, the mole ratio of the metallocene compound represented by Chemical Formula 1/the compound represented by Chemical Formula 3 is preferably 1/10,000~1/10, more preferably 1/5,000~1/100, and still more preferably 1/3,000~1/500. When the mole ratio is larger than 1/10, there is a problem of that the activity of the prepared catalyst composition is deteriorated because the activator is relatively small in quantity and the metal compound is not completely activated, and when the mole ratio is lesser than 1/10,000, the activation of the metal compound is completely accomplished but there is a problem of that the cost of the catalyst composition is not economical or the purity of the polymer prepared by using the same is decreased due to the remaining excess activator.

As the reaction solvent for preparing the catalyst composition, a hydrocarbon solvent such as pentane, hexane, heptane, and the like, or an aromatic solvent such as benzene, toluene, and the like may be used. Furthermore, the metallocene compound and the co-catalyst may be used in the form of that they are supported on silica or alumina.

The present invention also provides a method of preparing an olefinic polymer comprising the step of polymerizing olefinic monomers in the presence of the catalyst composition.

In the preparation method of the olefinic polymer according to the present invention, specific example of the olefinic monomer may be ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, and the like, it is also possible to copolymerize two or more monomers among them by mixture.

The olefinic polymer is preferably an ethylene/α-olefin copolymer, however, it is not limited to this.

In the case of that the olefinic polymer is the ethylene/α-olefin copolymer, the content of α-olefin, a comonomer, is not limited particularly, and it may be adequately selected according to the use or purpose of the olefinic polymer. More specifically, it may from over 0 mole % to 99 mole %.

The ethylene/α-olefin copolymer may be a multi-block copolymer comprising two or more segments or blocks of which chemical or physical characteristics are different.

In order to prepare the multi-block copolymer, a method of using two or more different transition catalysts and a chain shuttling agent has been known in the past. But, the method has a problem of that the process is complicated because it must use two or more different transition catalysts and a chain shuttling agent of a specific compound in the preparation of the multi-block copolymer, and the processibility is inferior because the molecular weight distribution (Mw/Mn) of the prepared multi-block copolymer is about 2.0, very narrow.

However, the present invention is characterized in that the olefin-based block copolymer can be simply prepared because it uses a single metallocene compound as the polymerization catalyst without using the chain shuttling agent. Furthermore, the prepared olefinic polymer is characterized in that it can have wide molecular weight distribution (Mw/Mn) and thus its processibility is excellent.

The present invention provides an olefinic block copolymer prepared according to the method disclosed above. Furthermore, the present invention provides an olefinic block copolymer, preferably an ethylene/α-olefin block copolymer, of which the melting temperature (Tm) is 100° C. or more.

In the present invention, the molecular weight distribution (Mw/Mn) of the olefinic polymer is preferably 2 or more, and more preferably 2.5 or more, however, it is not limited to this.

In the present invention, the weight average molecular weight (Mw) of the olefinic polymer may be 5,000~3,000,000, and preferably 5,000~1,000,000, however, it is not limited to this.

The density of the olefinic polymer may be 0.85 g/cm³~0.92 g/cm³, and preferably 0.85 g/cm³~0.90 g/cm³.

The olefinic polymer according to the present invention has a relatively high single or multi crystalline melting point in comparison to density of the polymer when measuring the melting point (Tm) with DSC. The melting point (Tm) of the olefinic polymer is preferably 100° C. or more irrespectively to the density of the polymer, and more preferably 105° C.~135° C., however, it is not limited to this.

In general ethylene/α-olefin block copolymer, as the content of comonomer in the copolymer increases, it shows a tendency of that the density of the copolymer and the melting point decrease. However, the olefinic copolymer according to the present invention can show the melting point of 100° C. or more even in the case of raising the content of the comonomer, and thus the polymer has not only thermal resistance but also superior mechanical strength.

Therefore, the olefinic polymer according to the present invention is superior in thermal resistance, mechanical strength, processability, and the like, and thus the olefinic polymer can be applied variously according to its use.

Hereinafter, the present invention provides preferable examples for illuminating the present invention. However, following examples are only for understanding the present invention, and the range of the present invention is not limited to or by them.

EXAMPLES

Preparation Example 1

1) Preparation of Ligand Compound

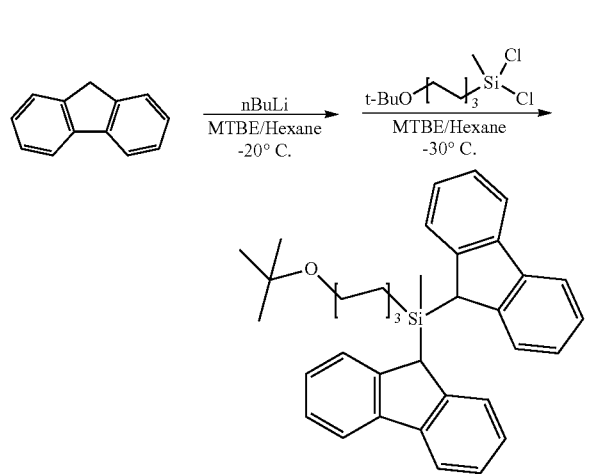

1.0 mole of tert-Bu-O—(CH$_2$)$_6$MgCl solution which is a Grignard reagent was obtained from the reaction between tert-Bu-O—(CH$_2$)$_6$Cl compound and Mg(0) in the presence of THF solvent. Tert-Bu-O—(CH$_2$)$_6$SiMeCl$_2$ (yield of 92%) was obtained by adding the prepared Grignard reagent into a flask in which MeSiCl$_3$ compound (176.1 mL, 1.5 mol) and THF (2.0 mL) of −30° C. were, stirring the solution for 8 hours or more at room temperature, and filtering and vacuum drying the solution.

After introducing fluorine (3.33 g, 20 mmol), hexane (100 mL), and MTBE (methyl tert-butyl ether, 1.2 mL, 10 mmol) into a reactor at −20° C., 8 ml of n-BuLi (2.5M in Hexane) was slowly added therein and the solution was stirred for 6 hours at room temperature. After the stirring was finished, the temperature of the reactor was cooled to −30° C., and the prepared fluorenyl lithium solution was slowly added to the tert-Bu-O—(CH$_2$)$_6$SiMeCl$_2$ (2.7 g, 10 mmol) dissolved in hexane (100 ml) at −30° C. for 1 hour. After stirring the same for 8 hours or more at room temperature, (tert-Bu-O—(CH$_2$)$_6$)MeSi(9-C$_3$H$_{10}$)$_2$ compound (5.3 g, yield of 100%) was obtained by extracting the same by adding water and evaporating the solvent. The structure of ligand was confirmed by $^1$H-NMR.

$^1$H NMR (500 MHz, CDCl$_3$): −0.35 (MeSi, 3H, s), 0.26 (Si—CH$_2$, 2H, m), 0.58 (CH$_2$, 2H, m), 0.95 (CH$_2$, 4H, m), 1.17 (tert-BuO, 9H, s), 1.29 (CH$_2$, 2H, m), 3.21 (tert-BuO-CH$_2$, 2H, t), 4.10 (Flu-9H, 2H, s), 7.25 (Flu-H, 4H, m), 7.35 (Flu-H, 4H, m), 7.40 (Flu-H, 4H, m), 7.85 (Flu-H, 4H, d).

2) Preparation of Metallocene Compound

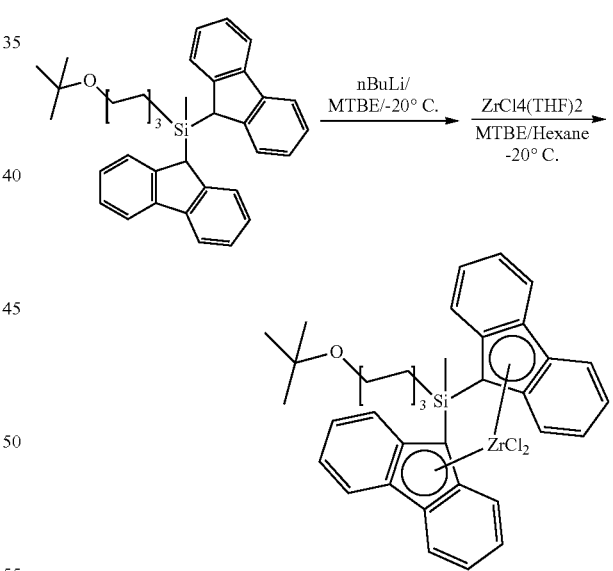

4.8 ml of n-BuLi (2.5M in Hexane) was slowly added to (tert-Bu-O—(CH$_2$)$_6$)MeSi(9-C$_{13}$H$_{10}$)$_2$ (3.18 g, 6 mmol)/MTBE (20 mL) solution at −20° C., and the solution was reacted for 8 hours or more with elevating the temperature to room temperature, and above dilithium salts slurry solution prepared at −20° C. was slowly added to ZrCl$_4$(THF)$_2$ (2.26 g, 6 mmol)/hexane (20 mL) slurry solution and the solution was further reacted for 8 hours at room temperature. (Tert-Bu-O—(CH$_2$)$_6$)MeSi(9-C$_{13}$H$_9$)$_2$ZrCl$_2$ compound (4.3 g, yield of 94.5%) of red solid form was obtained by filtering the precipitate and rinsing the same many times with hexane.

¹H NMR (500 MHz, C6D6): 1.15 (tert-BuO, 9H, s), 1.26 (MeSi, 3H, s), 1.58 (Si—CH2, 2H, m), 1.66 (CH2, 4H, m), 1.91 (CH2, 4H, m), 3.32 (tert-BuO-CH2, 2H, t), 6.86 (Flu-H, 2H, t), 6.90 (Flu-H, 2H, t), 7.15 (Flu-H, 4H, m), 7.60 (Flu-H, 4H, dd), 7.64 (Flu-H, 2H, d), 7.77 (Flu-H, 2H, d)

Preparation Example 2

1) Preparation of Ligand Compound (Tert-Bu-O—(CH₂)₄)MeSi(9-C₁₃H₁₀)₂ compound was obtained with the yield similar to Preparation Example 1 substantially according to the same method as in Preparation Example 1, except that tert-Bu-O—(CH₂)₄Cl compound was used in the preparation of ligand. The structure of ligand was confirmed by ¹H-NMR.

¹H NMR (500 MHz, C6D6): −0.40 (MeSi, 3H, s), 0.30 (CH₂, 2H, m), 0.71 (CH₂, 2H, m), 1.05 (tert-BuO, 9H, s), 1.20 (CH₂, 2H, m), 2.94 (tert-BuO-CH₂, 2H, t), 4.10 (Flu-9H, 2H, s), 7.16 (Flu-H, 4H, m), 7.35 (Flu-H, 4H, m), 7.35 (Flu-H, 2H, d), 7.43 (Flu-H, 2H, d), 7.77 (Flu-H, 4H, d).

2) Preparation of Methallocene Compound (Tert-Bu-O—(CH₂)₄)MeSi(9-C₁₃H₉)₂ZrCl₂ compound was obtained with similar yield substantially according to the same method as in Preparation Example 1, except that (tert-Bu-O—(CH₂)₄)MeSi(9-C₁₃H₁₀)₂ compound was used.

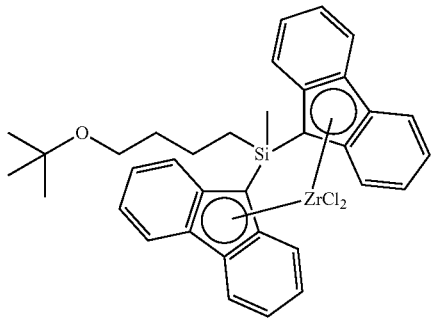

¹H NMR (500 MHz, C6D6): 1.14 (tert-BuO, 9H, s), 1.26 (MeSi, 3H, s), 1.90 (CH2, 2H, m), 1.99 (CH2, 2H, m), 2.05 (CH2, 2H, m), 3.39 (tert-BuO-CH2, 2H, t), 6.84 (Flu-H, 2H, m), 6.90 (Flu-H, 2H, m), 7.15 (Flu-H, 4H, m), 7.60 (Flu-H, 6H, d), 7.80 (Flu-H, 2H, d)

Preparation Example 3

1) Preparation of Ligand Compound (Tert-Bu-O—(CH₂)₈)MeSi(9-C₁₃H₁₀)₂ compound was obtained with the yield similar to Preparation Example 1 substantially according to the same method as in Preparation Example 1, except that tert-Bu-O—(CH₂)₈Cl compound was used in the preparation of ligand. The structure of ligand was confirmed by ¹H-NMR.

¹H NMR (500 MHz, C6D6): −0.40 (MeSi, 3H, s), 0.29 (CH₂, 2H, m), 0.58 (CH₂, 2H, m), 0.83 (CH₂, 2H, m), 0.95 (CH₂, 2H, m), 1.05 (CH₂, 2H, m), 1.14 (tert-BuO, 9H, s), 1.30 (CH₂, 2H, m), 1.64 (CH₂, 2H, m), 3.27 (tert-BuO-CH₂, 2H, t), 4.13 (Flu-9H, 2H, s), 7.17 (Flu-H, 4H, m), 7.26 (Flu-H, 4H, m), 7.37 (Flu-H, 2H, d), 7.43 (Flu-H, 2H, d), 7.78 (Flu-H, 4H, d).

2) Preparation of Methallocene Compound (Tert-Bu-O—(CH₂)₈)MeSi(9-C₁₃H₉)₂ZrCl₂ compound was obtained with similar yield substantially according to the same method as in Preparation Example 1, except that (tert-Bu-O—(CH₂)₈)MeSi(9-C₃H₁₀)₂ compound was used.

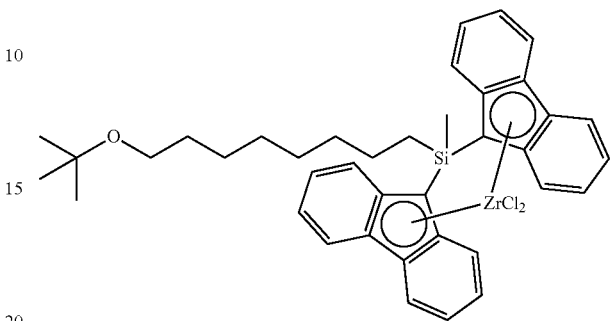

¹H NMR (500 MHz, C6D6): 1.17 (tert-BuO, 9H, s), 1.29 (MeSi, 3H, s), 1.41 (CH2, 4H, m), 1.49 (CH2, 2H, m), 1.64 (CH2, 2H, m), 1.89 (CH2, 4H, m), 1.94 (CH₂, 2H, m), 3.30 (tert-BuO-CH₂, 2H, t), 6.81 (Flu-H, 2H, m), 6.90 (Flu-H, 2H, m), 7.14 (Flu-H, 4H, m), 7.60 (Flu-H, 4H, d), 7.65 (Flu-H, 2H, d), 7.78 (Flu-H, 2H, d)

Example 1

After introducing 235 ml of toluene, 5 ml of 1-hexene, 10 ml of 10 wt % toluene solution of MAO into 500 ml glass reactor, 1 mM toluene solution (5 ml, 5 μmol) of the compound ((tert-Bu-O—(CH₂)₆)MeSi(9-C₁₃H₉)₂ZrCl₂) prepared in Preparation Example 1 was introduced into the solution, 50 psig of ethylene was introduced into the reactor, and the reaction was initiated. After stirring the solution for 0.5 hour and venting the reactor, the reaction product was poured into ethanol/hydrochloric acid solution. After stirring the solution and filtering and rinsing the product, the olefinic polymer was obtained by evaporating the solvent. The result is listed in following Table 1.

Example 2

The olefinic polymer was prepared substantially according to the same method as in Example 1, except that 10 ml of 1-hexene was introduced into the reactor. The result is listed in following Table 1.

Example 3

The olefinic polymer was prepared substantially according to the same method as in Example 1, except that 15 ml of 1-hexene was introduced into the reactor. The result is listed in following Table 1.

Examples 4, 5, 6

The olefinic polymer was prepared substantially according to the same method as in Example 1, except that 1-octene was introduced into the reactor in the amount of 6.3 ml, 12.6 ml, and 15.7 ml respectively. The results are listed in following Table 1.

Example 7

The olefinic polymer was prepared substantially according to the same method as in Example 1, except that the compound ((tert-Bu-O—(CH$_2$)$_4$)MeSi(9-C$_{13}$H$_9$)$_2$ZrCl$_2$) prepared in Preparation Example 2 was introduced as the metallocene compound. The result is listed in following Table 1.

Example 8

The olefinic polymer was prepared substantially according to the same method as in Example 1, except that the compound ((tert-Bu-O—(CH$_2$)$_8$)MeSi(9-C$_{13}$H$_9$)$_2$ZrCl$_2$) prepared in Preparation Example 3 was introduced as the metallocene compound. The result is listed in following Table 1.

Comparative Example 1

The olefinic polymer was prepared substantially according to the same method as in Example 1, except that traditional CGC catalyst represented by the following Chemical Formula was used. The result is listed in following Table 1.

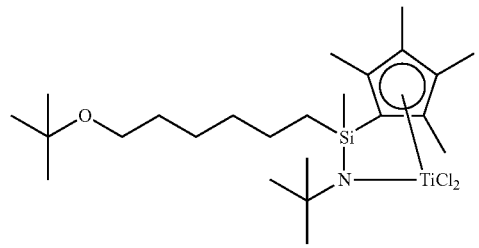

Comparative Examples 2, 3

The olefinic polymer was prepared substantially according to the same method as in Example 1, except that traditional metallocene catalyst represented by the following Chemical Formula was used and 1-hexene was introduced in the amount of 5 ml and 10 ml respectively. The results are listed in following Table 1.

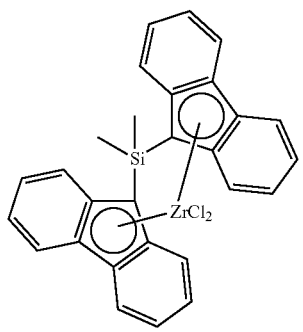

TABLE 1

| | Co-monomer (mol %) | Polymer (g) | Catalytic Activity (ton/mol · hr) | Tm (° C.) | Mw | PDI |
|---|---|---|---|---|---|---|
| Example 1 | 6.4 | 9.1 | 3.64 | 120 | 116,500 | 3.13 |
| Example 2 | 12.5 | 9.4 | 3.76 | 122 | 102,600 | 2.60 |
| Example 3 | 14.1 | 8.8 | 3.52 | 121 | 92,300 | 3.20 |
| Example 4 | 6.3 | 4.6 | 1.84 | 120 | 118,400 | 2.94 |
| Example 5 | 8.1 | 4.4 | 1.76 | 119 | 98,300 | 3.70 |
| Example 6 | 10.9 | 4.5 | 1.80 | 118 | 99,800 | 3.48 |
| Example 7 | 6.9 | 10.5 | 4.20 | 105-120 | 185,700 | 2.53 |
| Example 8 | 5.9 | 11.9 | 4.76 | 105-120 | 205,400 | 2.28 |
| Comparative Example 1 | 8.3 | 11.7 | 4.68 | 82 | 163,200 | 2.63 |
| Comparative Example 2 | 9.9 | 7.3 | 2.92 | 99 | 107,700 | 3.56 |
| Comparative Example 3 | 14.5 | 7.9 | 3.16 | 85 | 77,400 | 2.90 |

What is claimed is:

1. A metallocene compound represented by following Chemical Formula 1:

[Chemical Formula 1]

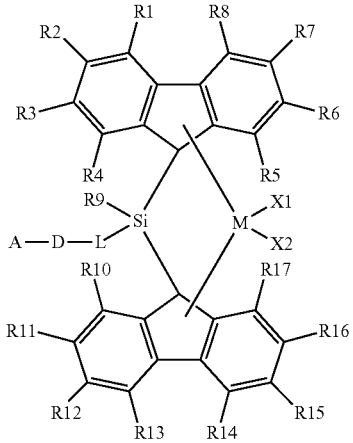

wherein,
each of R1 to R8 and R10 to R17 is, same or different from each other, a hydrogen, a C$_1$-C$_{20}$ alkyl group, or a C$_6$-C$_{20}$ aryl group,
R9 is methyl group,
L is a C$_4$-C$_{10}$ linear or branched alkylene group,
D is —O—,
A is tert-butyl group,
M is a group 4 transition metal, and
X1 and X2 are, same or different from each other.

2. The metallocene compound according to claim 1, wherein L in Chemical Formula 1 is a C$_4$~C$_8$ linear or branched alkylene group.

3. A catalyst composition, comprising the metallocene compound according to claim 1.

4. The catalyst composition according to claim 3, further comprising at least one co-catalysts represented by Chemical Formulae 3 to 5:

[Al(R18)-O$_n$]—  [Chemical Formula 3]

wherein,
each R18 is independently a halogen; a C$_1$~C$_{20}$ hydrocarbon; or a halogen-substituted C$_1$~C$_{20}$ hydrocarbon; and
n is an integer of 2 or more;

D(R18)$_3$  [Chemical Formula 4]

wherein,
R18 is same as that in Chemical Formula 3; and
D is aluminum or boron;

$$[L\text{-}H]^+[ZA_4]^- \text{ or } [L]^+[ZA_4]^- \qquad \text{[Chemical Formula 5]}$$

wherein,
L is a neutral or cationic Lewis acid;
H is hydrogen atom;
Z is group 13 element; and
each A is independently a $C_6$~$C_{20}$ aryl group or a $C_1$~$C_{20}$ alkyl group of which at least one hydrogen atom are unsubstituted or substituted with a halogen, a $C_1$~$C_{20}$ hydrocarbon, an alkoxy, or phenoxy.

\* \* \* \* \*